(12) United States Patent
McGhin et al.

(10) Patent No.: US 10,769,249 B2
(45) Date of Patent: Sep. 8, 2020

(54) DISTRIBUTOR PRODUCT PROGRAMMING SYSTEM

(71) Applicant: SANUWAVE, INC., Suwanee, GA (US)

(72) Inventors: Cary McGhin, Sugar Hill, GA (US); Iulian Cioanta, Milton, GA (US); Christopher Cashman, Johns Creek, GA (US); Clifford Martin, Alpharetta, GA (US)

(73) Assignee: SANUWAVE, INC., Suwanee, GA (US)

( * ) Notice: Subject to any disclaimer, the term of this patent is extended or adjusted under 35 U.S.C. 154(b) by 102 days.

(21) Appl. No.: 15/812,598

(22) Filed: Nov. 14, 2017

(65) Prior Publication Data
US 2018/0137260 A1    May 17, 2018

Related U.S. Application Data

(60) Provisional application No. 62/422,122, filed on Nov. 15, 2016.

(51) Int. Cl.
*G06F 21/86* (2013.01)
*G06F 21/31* (2013.01)
*G06F 21/10* (2013.01)
G06F 21/88 (2013.01)
G16H 40/67 (2018.01)
G16H 40/40 (2018.01)

(52) U.S. Cl.
CPC .... *G06F 21/105* (2013.01); *G06F 2221/0773* (2013.01); *G16H 40/40* (2018.01); *G16H 40/67* (2018.01)

(58) Field of Classification Search
None
See application file for complete search history.

(56) References Cited

U.S. PATENT DOCUMENTS 5,400,267 A  *  3/1995  Denen ............... A61B 17/00
                                                       128/908
6,186,963 B1    2/2001  Schwarze et al.
(Continued)

FOREIGN PATENT DOCUMENTS

| EP | 2 058 749 | 5/2009 |
|----|-----------|--------|
| EP | 3 070 627 | 6/2016 |
| WO | WO 2004/075092 | 9/2004 |

OTHER PUBLICATIONS

Notification of Transmittal of and the International Search Report and Written Opinion of the International Searching Authority, or the Declaration dated Feb. 9, 2018 by Blaine R. Copenheaver of ISA/US.

(Continued)

*Primary Examiner* — Venkat Perungavoor
(74) *Attorney, Agent, or Firm* — Polsinelli PC; Eric J. Hanson, Esq.

(57) ABSTRACT

A product programming system includes a product subject to maintenance, part refurbishment and/or part replacement that has a security device communicatively coupled to a computing device programmed to re-authorize normal operation of the product when a predetermined number of uses has been reached or a predetermined period of time has lapsed.

20 Claims, 8 Drawing Sheets

(56) References Cited

U.S. PATENT DOCUMENTS

| | | | |
|---|---|---|---|
| 6,237,604 B1* | 5/2001 | Burnside | A61B 90/90 128/897 |
| 2005/0113815 A1* | 5/2005 | Ritchie | A61B 18/20 606/15 |
| 2006/0217193 A1* | 9/2006 | Walker | G06Q 30/0218 463/29 |
| 2007/0156285 A1* | 7/2007 | Sillman | G16H 40/40 700/245 |
| 2007/0244825 A1 | 10/2007 | Semmer et al. | |
| 2008/0005000 A1* | 1/2008 | Radl | F04B 49/06 705/34 |
| 2008/0310864 A1* | 12/2008 | Katoh | G03G 15/5079 399/26 |
| 2013/0006154 A1 | 1/2013 | Lowe | |
| 2013/0012879 A1 | 1/2013 | Debelser et al. | |
| 2013/0212381 A1* | 8/2013 | Bousamra | H04L 63/0823 713/156 |
| 2013/0269700 A1* | 10/2013 | Laura Lapoint | A61B 5/0022 128/205.23 |
| 2014/0283011 A1 | 9/2014 | Orona et al. | |
| 2015/0377506 A1* | 12/2015 | Sakaguchi | G06F 11/00 700/276 |
| 2016/0243359 A1 | 8/2016 | Sharma | |
| 2016/0275251 A1* | 9/2016 | Ingmanson | A61B 17/07207 |

OTHER PUBLICATIONS

EP Patent Application 17871201.4, Extended European Search Report dated Jun. 15, 2020.

* cited by examiner

DISTRIBUTOR PRODUCT PROGRAMMING SYSTEM

CROSS-REFERENCE TO RELATED APPLICATIONS

The present application claims the benefit of priority of U.S. Provisional Application No. 62/422,122 filed Nov. 15, 2016, which is incorporated herein by reference.

BACKGROUND OF THE INVENTION

A system is needed that enables a manufacturer to control or regulate the ability of the manufacturer's distributor to refurbish, or service, or produce the manufacturer's product, such that without controlled authorization from the manufacturer, either through a distributor license or a networked computer system controlled by the manufacturer, the distributor is incapable of performing the required support processes related to the manufacturer's product. The distributor authorization from the manufacturer when using a networked computer system can be accomplished by the manufacturer's remote application server that provides a remote desktop session for the distributor to have access to the software application that enables the distributor to perform the product services. An alternative is the distributor is operating a local custom software application on their local computer, and authorization to perform the product services is done through periodic communication with the manufacturer's server.

The common benefit of the distributor license or networked authorization system is that the manufacturer can track and audit all maintenance, refurbishments, reprocessing, repair services, or production activities performed by the distributor and use the information for revenue sharing from the distributor product activities.

The networked authorization system has additional benefits of stopping distributor product services instantly if required, and the manufacturer can access product information that the distributor collects in real time during each product activity performed by the distributor. The manufacturer can electronically track materials (via bar-coding, RFID identification, etc.) being utilized by the distributor to perform the maintenance, reprocessing or servicing, or during production and facilitate remote inventory management. The other benefit of real time network data exchange would be in products that store a history record each time it is used; the stored information could be uploaded from the distributor to the manufacturer during maintenance or service repair.

DETAILED DESCRIPTION OF THE INVENTION

The primary mechanism for this application is a system that in order to perform product or accessory maintenance or service requires a proprietary interface to the system only known by the manufacturer. One type of mechanism is a security device built into the manufacturer's product or accessory that functions to track the number of times it is utilized in the field. Once the useful life of the product or accessory has been reached, the security device will prevent the product or accessory from being further used until the security device can be provided reset instructions, which will occur during servicing or repair by the manufacturer's distributor or authorized service provider. To control and monitor the service activity by the manufacturer's distributor there are two proposed embodiments, the $1^{st}$ embodiment is the manufacturer provides a custom hardware unit and a custom software application to the distributor that is installed on the distributor's local computer. The custom hardware unit, during product service or production, provides the physical interface in the form of a direct electrical connection or wireless connection to the security device incorporated in the manufacturer's product or accessory. The custom hardware unit contains a secure license storage media to store an electronic license file and prevent its unauthorized access. The license is only accessible through the manufacturer supplied software application that operates the distributor's local computer being used to perform the service or production. The license grants the distributor a limited number of products to service or produce, where the security device is reset during either of these activities. The $2^{nd}$ embodiment includes a networked computer system between the manufacturer and the distributor's local computer. The distributor's local computer would be operated with a manufacturer supplied custom software application that automatically connects to the manufacturer's server, using a wide area network (WAN) such as the internet, to obtain authorization to perform the product or product accessory security device reset. An alternative to the $2^{nd}$ embodiment is a manufacturer's remote application server that provides a remote desktop with the application session for the distributor to access that enables the distributor to perform the security device service or production related processes. As in the $1^{st}$ embodiment a custom hardware unit connects to the distributor's local computer to provide the physical interface to the security device contained in the manufacturer's product or accessory.

In both embodiments the custom hardware unit, which will be known as the product programming interface unit, provides a proprietary interface to the security device contained in the manufacturer's product or accessory. The security device for example can be a SIM card, secure memory device, security key, etc. The proprietary interface can be either a cable connection, direct signal connection, RFID, cellular network, GPS, or other wired or wireless means and connections to re-initialize the security device and thus enabling the product or accessory for its intended use and normal operation. If the distributor is unable to gain authorization, either through a valid license or authorization from the manufacturer's network computer, the product security device will act as an interlock preventing the product or accessory from being used by the end customer for its intended purpose and normal operation.

As an example, the manufacturer is producing a product or product accessory that requires occasional or a periodic maintenance or part refurbishment or part replacement so that its performance during application remains at an optimal level. A secure memory device (SIM card) is incorporated into the product or product accessory that the system uses to maintain a counter or counters to track the number of application uses. Once the counter or combination of counters expire, continued use of the product or product accessory is prohibited, i.e., normal operation is disabled, by built in system controls within the product or product accessory. It will then require that the counter or counters be reset through service authorization to have continued use of the product or product accessory by the customer.

In both embodiments, the distributor's site will utilize a Distributor Product Programming System (or "DPPS") for performing the reset of the secure memory device during production, service, or refurbishment of the product or product accessory. The DPPS includes a workstation that operates using a custom DPPS software application, and a product programming interface unit, that together are used to reset the secure memory device contained in the product or product accessory.

In some embodiments, the product or product accessory may be a medical treatment device or treatment accessory. As an example, a shock wave applicator for medical treatment, such as described for example in U.S. Pat. No. 6,186,963, incorporated herein by reference, includes electrodes and a fluid volume with catalyst material that requires maintenance for optimal performance. After numbers of uses, i.e. spark discharges, the performance of the shock wave applicator will be affected and require fluid replacement, electrode refurbishment and/or part replacement to ensure proper performance of the applicator. A security device, such as SIM card, may be included in the applicator and provide a predetermined number of uses before connection to computing device, via a proprietary communication interface, is required to reset and authorize the applicator as part of the required maintenance, refurbishment and/or replacement. The systems and methods described herein will be appreciated as adapted to such example of product programming and maintenance control for not only a shock wave applicator, but to other medical devices and products.

Figure 1:
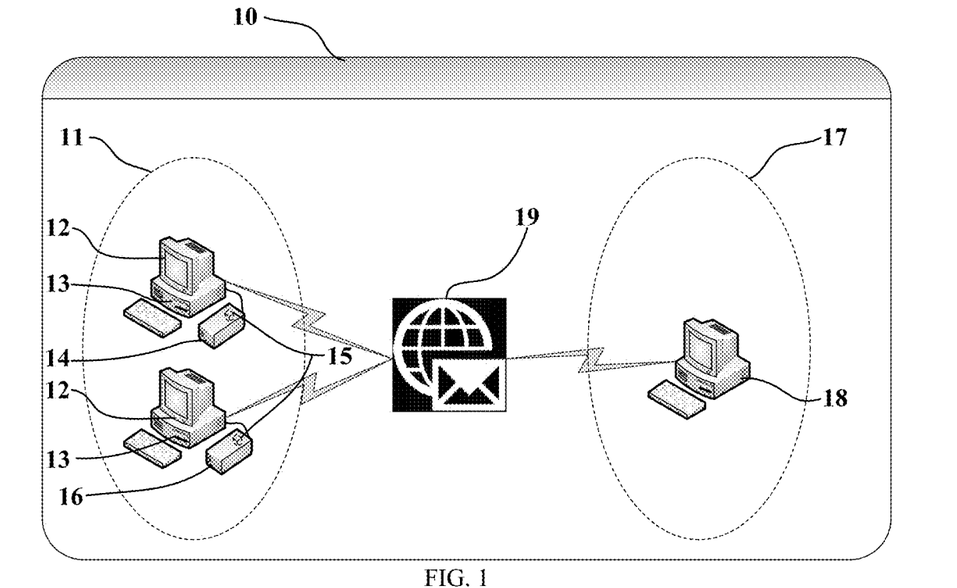
FIG. 1 is a schematic diagram of a licensed controlled distributor product programming system in one embodiment of the present invention.

In FIG. 1 a license controlled Distributor Product Programming System (DPPS) 10 is described. In this embodiment, it includes two distributor workstations 12 connected to separate product programming interface units 14 and 16 with both internally containing a license file that is stored on the license secure storage media 15 they both contain. The configuration depicted in FIG. 1, as an example, allows the distributor to process two of the manufacturer's products or accessories containing the secure memory devices simultaneously, however there is no limit to the number distributor workstations 12 and product programming interface units, like 14 and 16, that the distributor can simultaneously operate to perform the product or product accessory service and production provided that each one has their own unique valid license.

For the distributor to perform service, refurbishment, or production of the product or product accessory, the distributor must have a valid license. A unique license is required for each product programming interface unit 14 and 16. The license file is encrypted and stored on the license secure storage media 15 that is built into each product programming interface unit 14 and 16. The license secure storage media 15 normally remains locked or inaccessible, and can only be accessed through the DPPS software application 13. The licensed DPPS software application 13 contains the unlock protocol to access the license.

In FIG. 1 to access the secured and encrypted license file from the license secure storage media 15 requires using the connected distributor's workstation 12, operating with the licensed DPPS software application 13, and a connection to the product programming interface unit 14 or 16. The secured and encrypted license file contains a process limit on the number of service or production devices i.e. secure memory devices that are allowed for the distributor 11 to process. The licensed DPPS software application 13 will maintain the number of service and production occurrences within the license and compare it to the license limit, otherwise known as a process or transaction limit. The license transaction limit will act as the limited authorization controlled by the manufacturer. If the transaction limit has not been reached, the licensed DPPS software application 13 will enable the distributor 11 to reset the secure memory device of the product or product accessory during service, refurbishment, or manufacturing. To interface to the secure memory device of the product or product accessory, the embodiment In FIG. 1 provides a means to either engage the product or product accessory into product programming interface unit 14 or 16 when a direct electrical contact is required, or place the product or product accessory in the local vicinity of the product programming interface unit 14 or 16 when a wireless data transaction occurs with the secure memory device.

In an embodiment shown in FIG. 1, once the transaction limit of the license has been reached, the license is expired and requires the manufacturer 17 in FIG. 1 supply a new encrypted license file, which is generated by the manufacturer's license generating workstation 18, to the distributor's workstation 12 via electronic mail 19. In other embodiments the distributor's license file may be updated by other electronic download and transmission techniques known in the art. Upon receipt of the new encrypted license file, the distributor 11 downloads the encrypted license file to the license secure storage media 15 of the respective product programming interface unit 14 or 16 using the custom licensed DPPS software application 13 operating the distributor's workstation 12.

Figure 2:
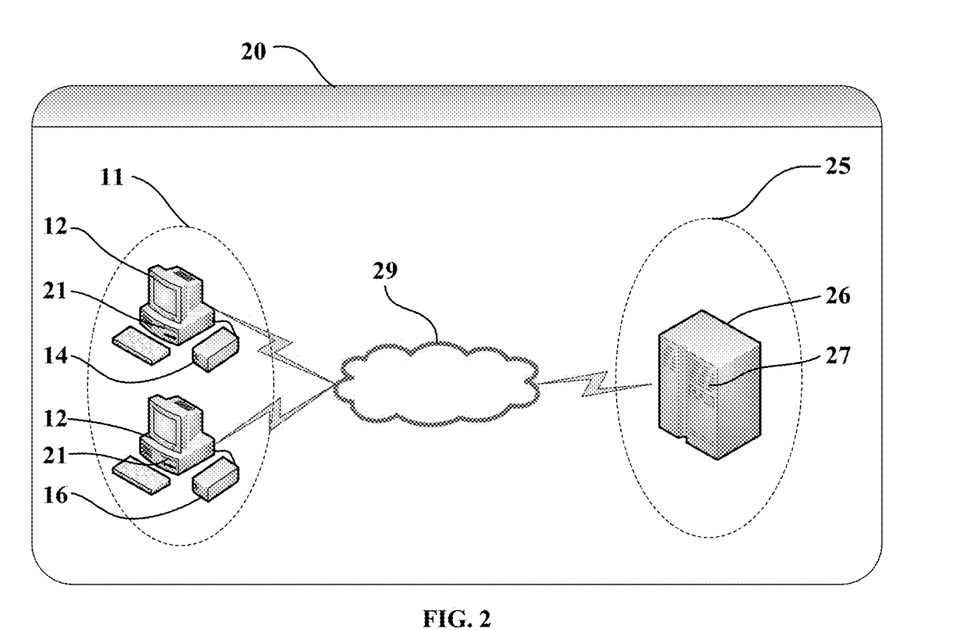
FIG. 2 is a schematic diagram of a network controlled distributor product programming system in one embodiment of the present invention.

In FIG. 2 is the other embodiment is a network controlled DPPS 20. There are two main subsystems, the first is a DPPS workstation 12 operating with a custom network DPPS software application 21. The DPPS workstation 12 is connected to the product programming interface unit 14 or 16 needed to interface to the secure memory device contained in the manufacture's product or accessory. This first subsystem will reside at the distributor's 11 refurbishment/service/production site, and connects to the internet 29 for communication with the other subsystem, which is the DPPS authorization and reporting server 26. The DPPS authorization and reporting server 26 can reside either at the manufacturer 17 or the manufacturer supported cloud based service site 25. The configuration depicted in FIG. 2, can be setup for multiple distributors all controlled by the same DPPS authorization and reporting server 26. The number of DPPS workstations 12 and product programming interface units 14 and 16 can also be increased to allow the distributor(s) to service or produce multiple products or product accessories i.e. secure memory devices simultaneously.

The general state flow in FIG. 2 is the DPPS workstation 12 requests by internet 29 connection with the authorization and reporting server 26, the authorization to perform the service or production of the product or product accessory. The authorization and reporting server 26 under the control of a custom DPPS server software application 27 authenticates and if successful authorizes the request. As in FIG. 1 the DPPS workstation 12 combined with the product programming interface unit 14 or 16 provides the physical interface to the secure memory device of the manufacturer's product or product accessory. The DPPS authorization and reporting server 26 can also collect from the DPPS workstation 12, via the internet 29, the product use information that is retained by the manufacturer's product media associated with each product or product accessory. The DPPS Workstation 12 operating from a network DPPS software application 21, together with product programming interface unit 14 or 16 will be used to reset the secure memory device of the product or product accessory.

Figure 3:
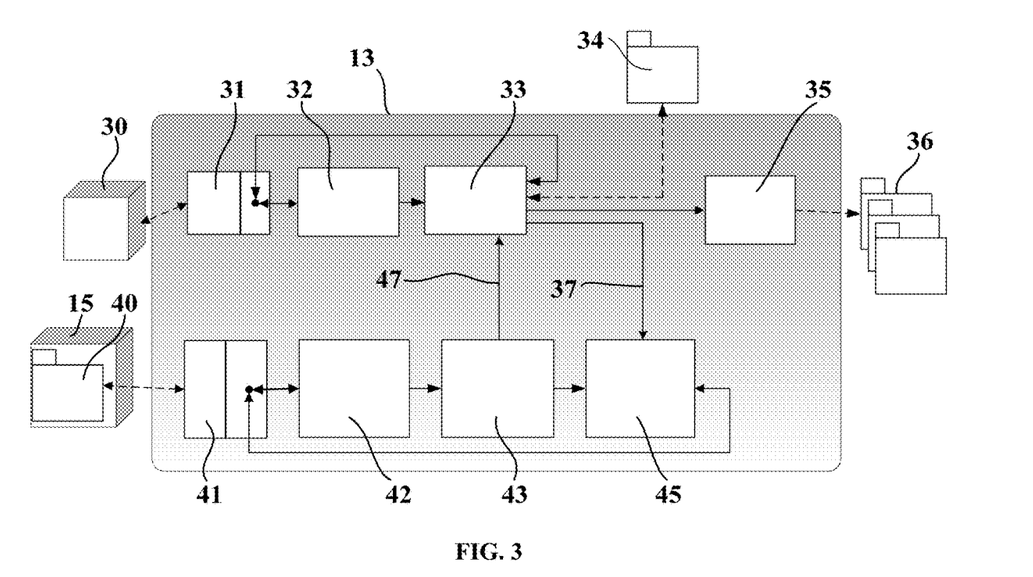
FIG. 3 is a state flow diagram of software and interfaces of a licensed controlled distributor product programming system in one embodiment of the present invention.

FIG. 3 is a state flow diagram of the licensed DPPS software application 13 referred to in FIG. 1. The licensed DPPS software application 13 of FIG. 3 during execution manages two parallel operational state flows. The first operational state flow is authenticating the license secure storage media 15 of FIG. 1, so that the secure and encrypted license file 40 of FIG. 3 can be accessed and modified. The second operational state flow is authenticating and updating the manufacturer's secure product media 30 of FIG. 3, which can be referred to as a security device, secure memory device, or any secure media, etc., that is physically located on the manufacturer's product or product accessory.

The second operational state flow of authenticating and updating the manufacturer's secure product media 30 will be discussed first. The product media data transfer phase 31 in FIG. 3 provides the bidirectional communication protocol with the manufacturer's secure product media 30. The product media authentication phase 32 performs the authentication sequence through the product media data transfer phase 31 to unlock the manufacturer's secure product media 30 and retrieve the unlocked memory device information. If the license file authentication status 47 is valid, the product media process control phase 33 is enabled to modify i.e. reset the manufacturer's secure product media 30 contents. The contents can be, but is not limited to:

A counter or counters that track the number of applications of the product or accessory by the customer A record of the product or accessory configuration including the date and time the product or accessory was used.

The product media process control phase 33 uses the licensed DPPS product media configuration file 34 to define the parameter and parameter values for creating or modifying the manufacturer's different product media. The product media process control phase 33 communicates bidirectionally with the product media data transfer phase 31 to validate the modified media. The product media process control phase 33 reports the product media process status 37 to the license update and encryption phase 45. A successful product media process status 37 would result in adjusting the license transaction counter value for the license so that it essentially reduces the number of future product accessory services and/or device production by one. The successful written data from the product media process control phase 33 is communicated to the product media reporting phase 35, which formats the output into different reports that are visible on the display of the distributor workstations 12, and are saved as service and production records and product application history files 36 on the distributor workstations 12.

The other process states of FIG. 3 that authenticate and update the secure and encrypted license file 40 is now described. To read the encrypted license file 40 requires that it be unlocked or released by the license secure storage media 15 of FIG. 1. The license authentication phase 42 in FIG. 3 provides the authentication sequence through the license data transfer phase 41 to unlock the license secure storage media 15 so that the encrypted license file 40 can be read and processed. The license data transfer phase 41 transfers the unlocked encrypted license to the license authentication phase 42 as a data packet for further authentication. If the encrypted license is authentic, it is transferred to the license decryption phase 43, which separates the individual elements of the encrypted license data packet into intelligible values and determines that the element values are valid. Some of the elements of the license are a unique product programming interface unit identification number, the transaction counter value, and the license issue number. If the license element values are valid, the license authentication status 47 enables the product media process control phase 33 to operate. Without the license authentication status 47, the DPPS software and i.e. the distributor is locked out from updating i.e. resetting the counter or counters of the manufacturer's secure product media 30. The product media process status 37 is reported back to the license update and encryption phase 45 so that it can adjust the license transaction counter value, which is part of the license, if the programming of the manufacturer's secure product media 30 was successful. The encryption portion of the license update and encryption phase 45 will encrypt all the data element values of the license and compact into a single encrypted data packet. The license data transfer phase 41 updates the encrypted license file 40 with the newly encrypted data packet.

Figure 4:
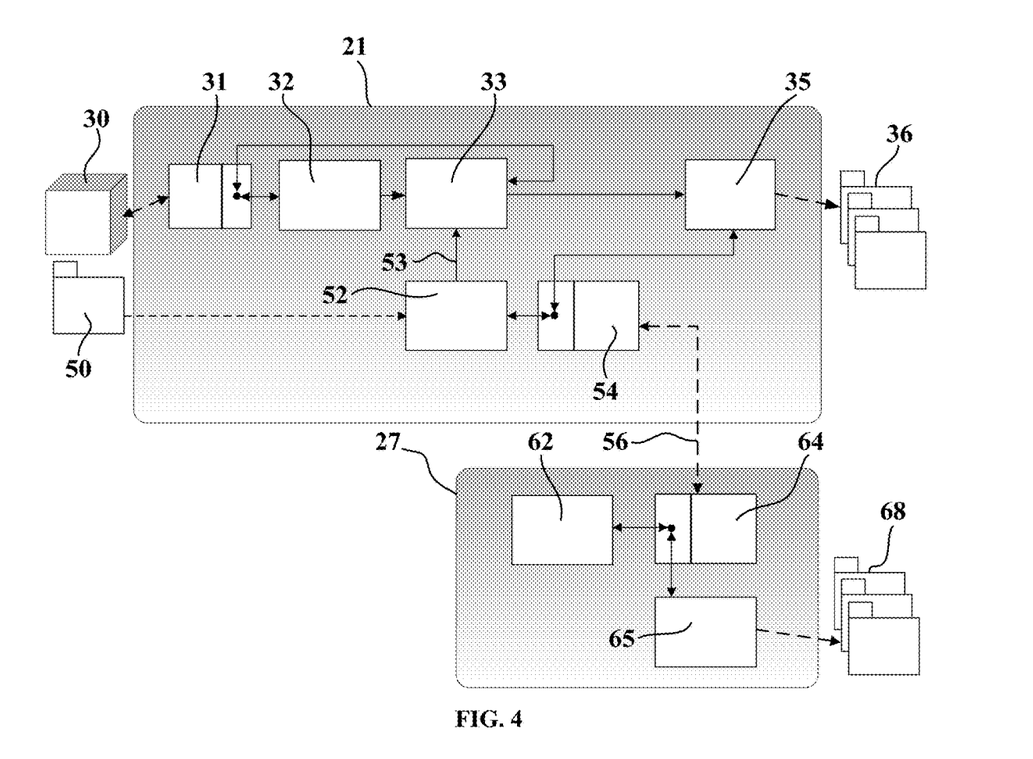
FIG. 4 is a state flow diagram of software and interfaces of a network controlled distributor product programming system in one embodiment of the present invention.

FIG. 4 illustrates the state flow of the network DPPS software application 21 for the network controlled DPPS 20 in FIG. 2. The ability for the distributor to service or produce the manufacturer's secure product media 30 contained in the product or product accessory requires that the server authorization phase 62 of the DPPS server software application 27 approve it. The server authorization phase 62 begins by performing an authentication protocol through the server data transfer phase 64 to the network DPPS data transfer phase 54 and on to network DPPS authorization phase 52. The authentication information is retrieved in part from the networked DPPS operational data file 50 and from the server authorization phase 62, which the later will provide new operational data through the network DPPS authorization phase 52. The server data transfer phase 64 and the network DPPS data transfer phase 54 are each responsible for performing all network bidirectional data communication 56 between the DPPS server software application 27 and the network DPPS software application 21, respectively. The network DPPS authorization phase 52 must provide the proper authentication sequence to be granted authorization. Additionally, the authorization is based on criteria within the DPPS server software application 27 that is used to control the number of service and or production transactions i.e. product or product accessories processed by the distributor. Examples are:

a process quantity limit date controlled limit terminated at will by the manufacturer The server reporting phase 65 of FIG. 4 collects the distributor service and production history as well as field application history from the product media reporting phase 35 using the server data transfer phase 64 and the network DPPS data transfer phase 54, respectively. The server reporting phase 65 generates a distributor data base 68 for the manufacturer to monitor each distributor that are part of the manufacturer's distributor network.

The product media data transfer phase 31 in FIG. 4 provides the bidirectional communication protocol with the manufacturer's secure product media 30. The product media authentication phase 32 performs the authentication sequence through the product media data transfer phase 31 to unlock the manufacturer's secure product media 30 and retrieve the unlocked memory information. The server authorization phase 62 grants authorization to the product media process control phase 33, via the network bidirectional data communication 56, to program i.e. reset the counter or counters of the manufacturer's secure product media 30. The product media process control phase 33 communicates to the manufacturer's secure product media 30 using the product media data transfer phase 31 to update and validate the manufacturer's secure product media 30 contents. The product media process control phase 33 reports the result to the product media reporting phase 35, which formats the output into different reports that are saved as service and production records and product application history files 36 on the distributor workstations 12. The product media reporting phase 35 can also report the same information to the DPPS authorization and reporting server 26 through the network DPPS data transfer phase 54.

Figure 5:
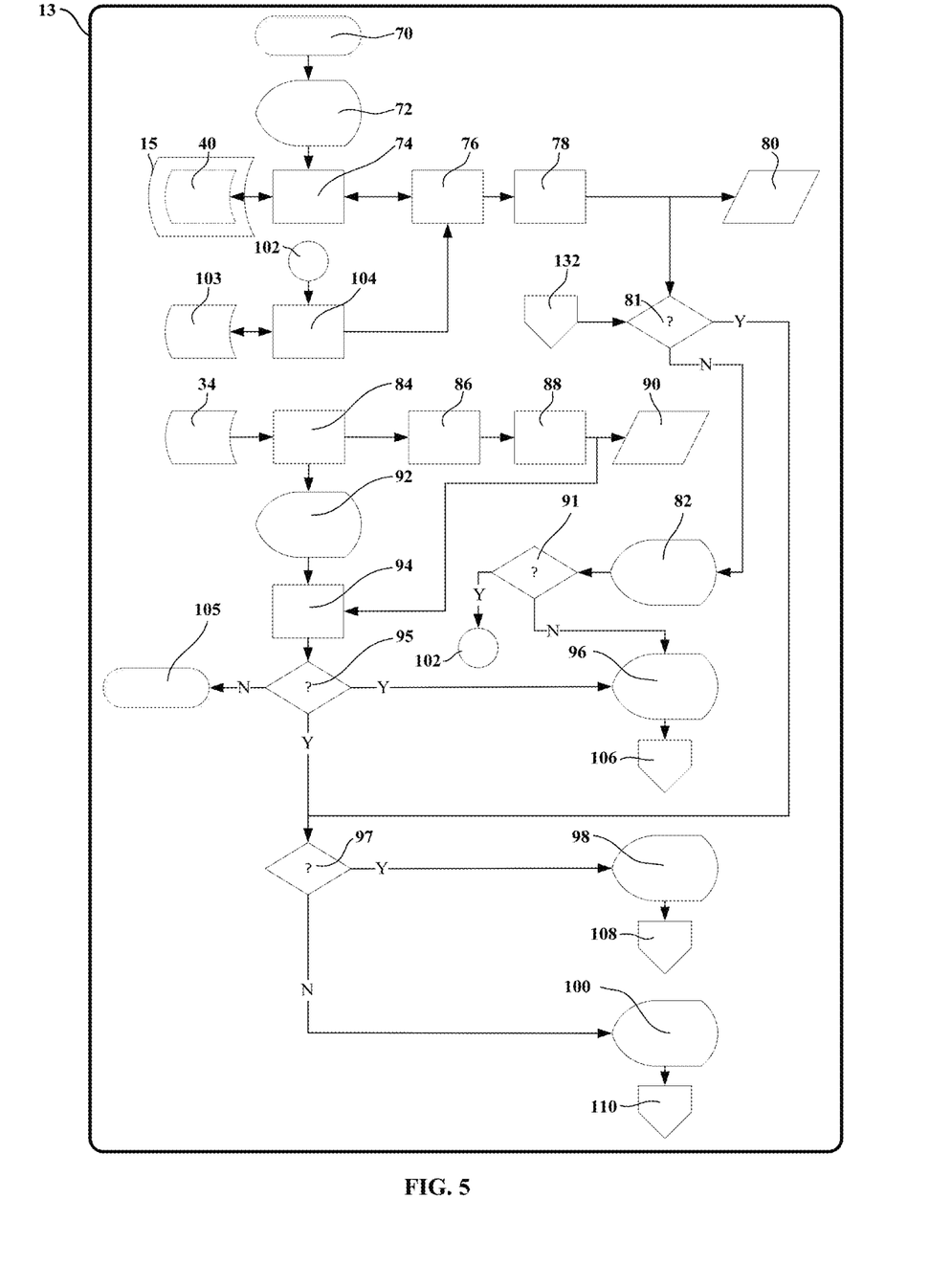
FIG. 5 is a software process flow diagram of special application software operating a distributor's computer used in a licensed distributor product programming system that is related to startup, license access and processing, and user login in one embodiment of the present invention.

FIG. 5 describes details of the software process flow for the licensed DPPS software application 13 from FIG. 3. In this section, the processes related to the license are described. The licensed DPPS software application start process 70 by presenting the licensed DPPS application welcome screen 72 to the user. The application's license file data transfer process 74 is the communication interface to the license secure storage media 15. To read the encrypted license file 40 requires that it first be unlocked from the license secure storage media 15. The authenticate license process 76 provides the protocol required to unlock the license. Once the license is unlocked, the decrypt license process 78 deciphers the license into the license elements 80 for use by the application. Some of the license elements are, but is not limited to:

the unique distributors machine identification the license issue number a process quantity limit (transaction limit) for the number of manufacturer's products where service or maintenance has been performed inclusively or separately a production quantity limit of the manufacturer's products or accessories produced by the distributor a license expiration period The condition of a valid license that is not expired 81, i.e. the distributor transaction limit has not been reached, enables the user to update or create the manufacturer's secure product media 30 based on their login access level 97. A license that is not valid or expired results in the licensed DPPS software application 13 displaying the upload new license prompt 82. If the user elects to upload a new license 91, the upload new license process 104 via 102 prompts the user to select the location and filename of new encrypted license file 103. The assumption here is that the new encrypted license file 103 has already been provide by the manufacturer via electronic mail or transfer as described for FIG. 3. After the user enters the new encrypted license file 103 location information, the upload new license process 104 transfers the file to the authenticate license process 76. The authenticate license process 76 must first unlock the license secure storage media 15, as described earlier, before the new encrypted license file 40 can be saved to the license secure storage media 15. If the user elects not to upload a new license 91, the application restricts the manufacturer's secure product media 30 access to a read-only interface 96 that allows the user to only read from the manufacturer's secure product media 30 of FIG. 3. The off-page reference to read manufacture's secure media 106 in FIG. 5 provides a process flow connection to the same off-page reference 106 in FIG. 6 where the process is described further.

In this section, the software process flow in FIG. 5 related to user login and user access privilege processing for the licensed DPPS software application 13 is described. The licensed DPPS application display login 92 requests the user to set the user access level, as either a general user or a super-user, and provide the required login password under the control of the licensed DPPS application login process 94. A valid login entry 95, results in then checking the user access level 97 to determine if the application screen should present the super-user interface 98, which allows the user to create and update the manufacturer's secure product media 30 of FIG. 3, or present the general user interface 100 that allows only the update of the manufacturer's secure product media 30 (both discussed in FIG. 6). An invalid login entry 95, results in the termination 105 of the licensed DPPS software application 13 of FIG. 3. The processes associated with the super-user interface 98 and the general user interface 100 will be described later in the definition of FIG. 6. The (off-page) reference to create manufacture's secure product media 108 and reference to update manufacture's secure media 110 in FIG. 5 provide the process flow connections to the same off-page references 108 and 110 in FIG. 6, which the later describes the processes related to the super-user or general user, respectively.

In FIG. 5 to create or update the manufacturer's secure product media 30 requires that the licensed DPPS product media configuration file 34 be uploaded into the licensed DPPS application. The licensed DPPS product media configuration file 34 is stored as encrypted information. The media contents are extracted by the read licensed media configuration process 84, which then forwards the read information to the decrypt licensed media configuration process 86. The encrypted licensed media configuration information is deciphered by the decryption process and then organized into useable elements by the store licensed media configuration elements process 88 that saves the elements to the licensed temporary configuration data 90. Some of the licensed temporary configuration data 90 elements include the valid user levels, user names, and password information, which is used by the licensed DPPS application login process 94.

Figure 6:
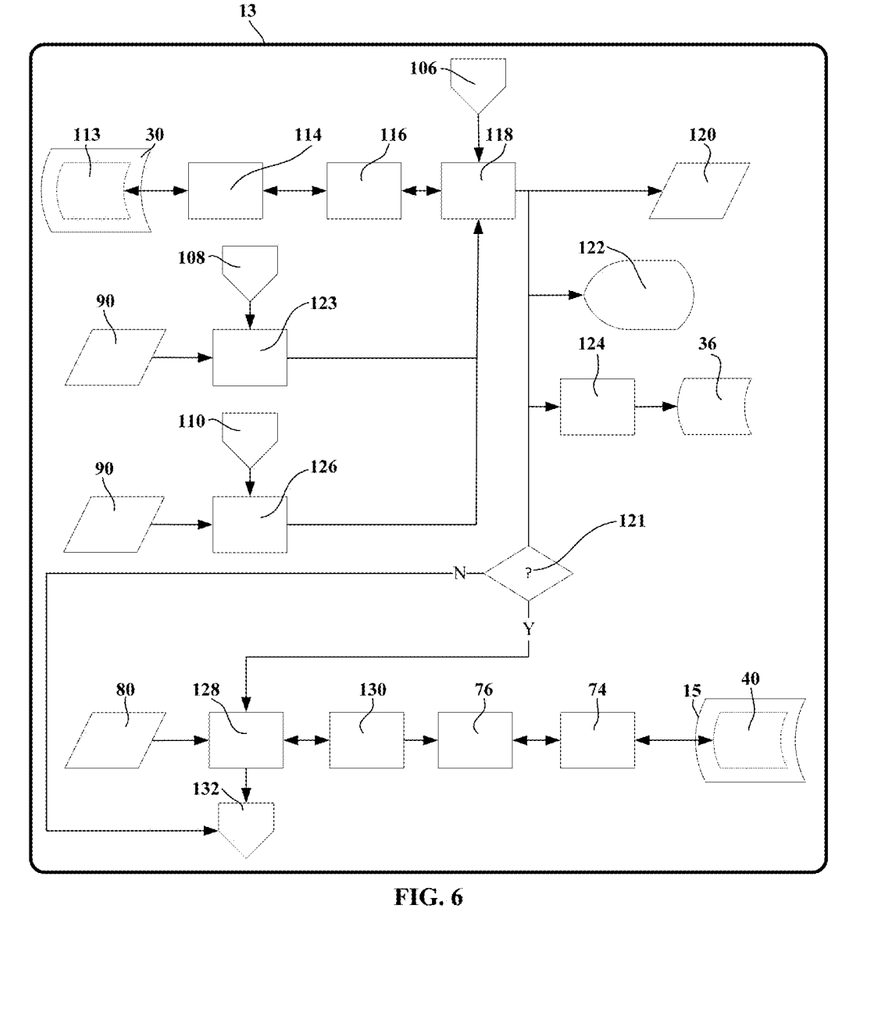
FIG. 6 is a software process flow of special application software operating a distributor's computer used in a licensed distributor product programming system related to access of the manufacturer's secure product media and updating the license in one embodiment of the present invention.

In FIG. 6 the software processes that interface to the manufacturer's secure product media 30, which originated from the off-page references 106, 108, and 110 of FIG. 5 will now be described. The product media data interface process 118 controls the process of reading from, or creating or updating the manufacturer's product media data 113 that is contained within the manufacturer's secure product media 30. It also updates the contents of the product media temporary storage 120, and lastly formats and presents the information on the media data display screen 122. Any data transaction with the manufacturer's secure product media 30 is recorded by the format product media data to database process 124 and writes the result to the service and production records and product application history files 36. The manufacturer's secure product media 30 in this example is a secured storage media device that requires authentication to access or update its contents. The authenticate product media process 116, by way of control from the product media data interface process 118, removes the security data lock. The product media data transfer process 114 controls the communication between the manufacturer's secure product media 30 and the licensed DPPS software application 13. Once the manufacturer's secure product media 30 is unlocked, access to the manufacturer's product media data 113 for reading or writing to the media is granted. The process of just reading the manufacturer's product media data 113 is initiated by the off-page reference 106 that originated from FIG. 5. The process of creating i.e. producing the manufacturer's secure product media 30 and data 113 comes from the off-page reference 108 that originated from FIG. 5. Using the product media data interface process 118, the authenticate product media process 116 unlocks the manufacturer's secure product media 30 and confirms that it is a new but compatible media device. After verifying the new manufacturer's secure product media 30, the initialize product media process 124 writes the initialization information, read from the licensed temporary configuration data 90, to create a functional manufacturer's secure product media 30. The process of updating the manufacturer's secure product media 30 comes from the off-page references 110 that originated from FIG. 5. Using the product media data interface process 118, the authenticate product media process 116 unlocks the manufacturer's secure product media 30 and confirms that it is a valid media device. After authentication and verification of the manufacturer's secure product media 30 occurs, the program product media process 126 writes the information, read from the licensed temporary configuration data 90, to the manufacturer's secure product media 30.

In FIG. 6 the processes of creating or updating the manufacturer's secure product media 30 requires updating the license transaction counter(s). The license transaction counter(s) can be multiple limit counters to distinguish distributor service processes from distributor production processes related to the manufacturer's secure product media 30. In either case if the product media process status 121 indicates that the manufacturer's secure product media 30 has been updated or created, the respective license transaction counter is updated using the adjust license transaction counter process 128. If the transaction counter limit has been reached, the off-page reference 132 directs the processing back to FIG. 5. The license elements 80 that was derived from FIG. 5 provides the current transaction counter value(s) that the license transaction counter adjustment process 128 needs for processing. The license elements that now include the adjusted license transaction counter(s) are encrypted into a compacted string by the encrypt license process 130. To write the new encrypted license to the license secure storage media 15, the authenticate license process 76 must first unlock the license secure storage media 15 using the license file data transfer process 74 as the communication interface to the license secure storage media 15. Once the license secure storage media 15 is unlocked the new license is written and following that the media is secured again.

Figure 7:
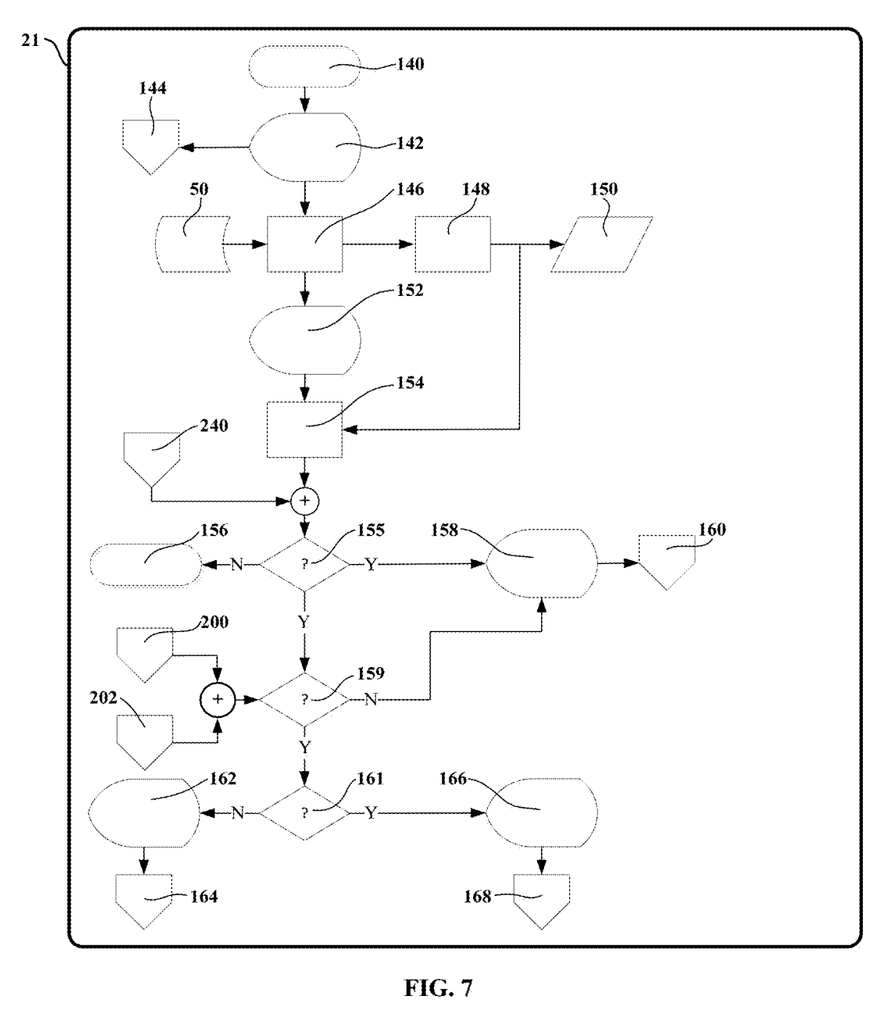
FIG. 7 is a software process flow of special application software operating a distributor's computer used in a networked distributor product programming system that is related to startup and user login in one embodiment of the present invention.
Figure 8:
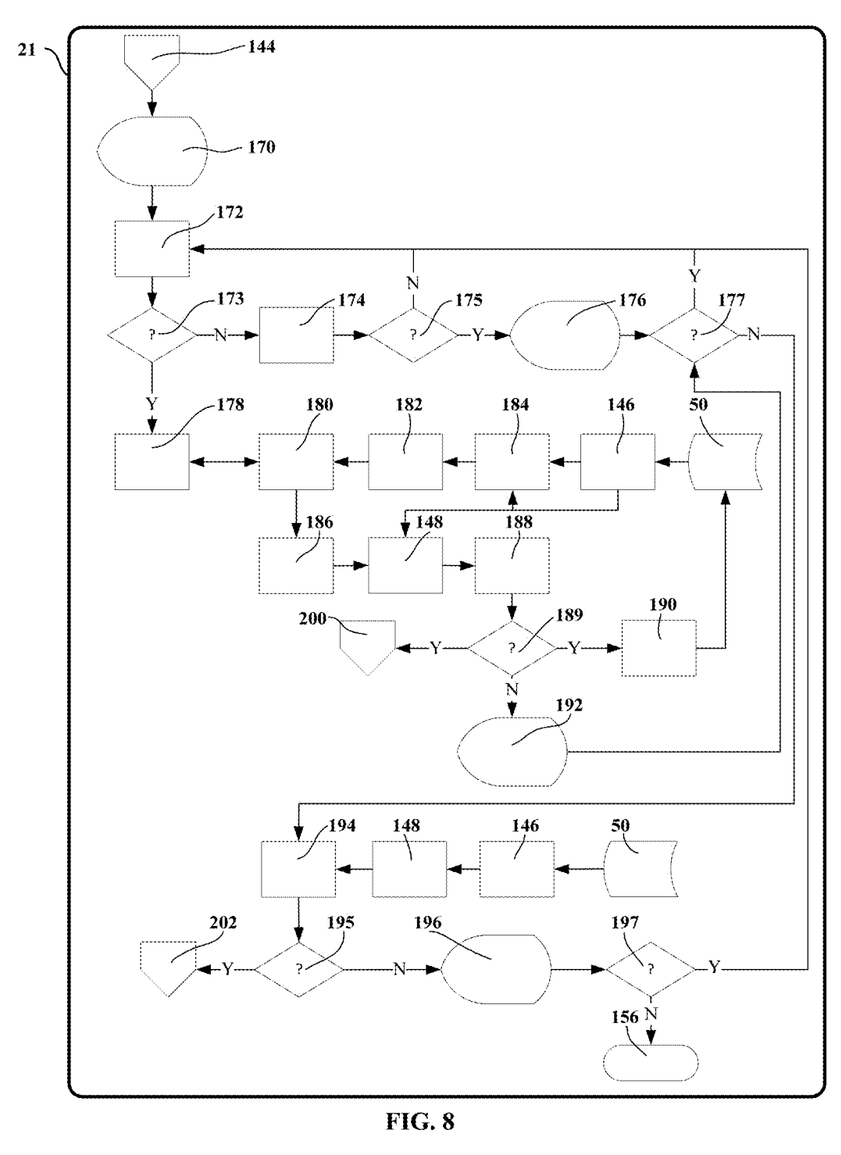
FIG. 8 is a software process flow of special application software operating a distributor's computer used in a networked distributor product programming system that is related to network connection to the manufacturer's server in one embodiment of the present invention.
Figure 9:
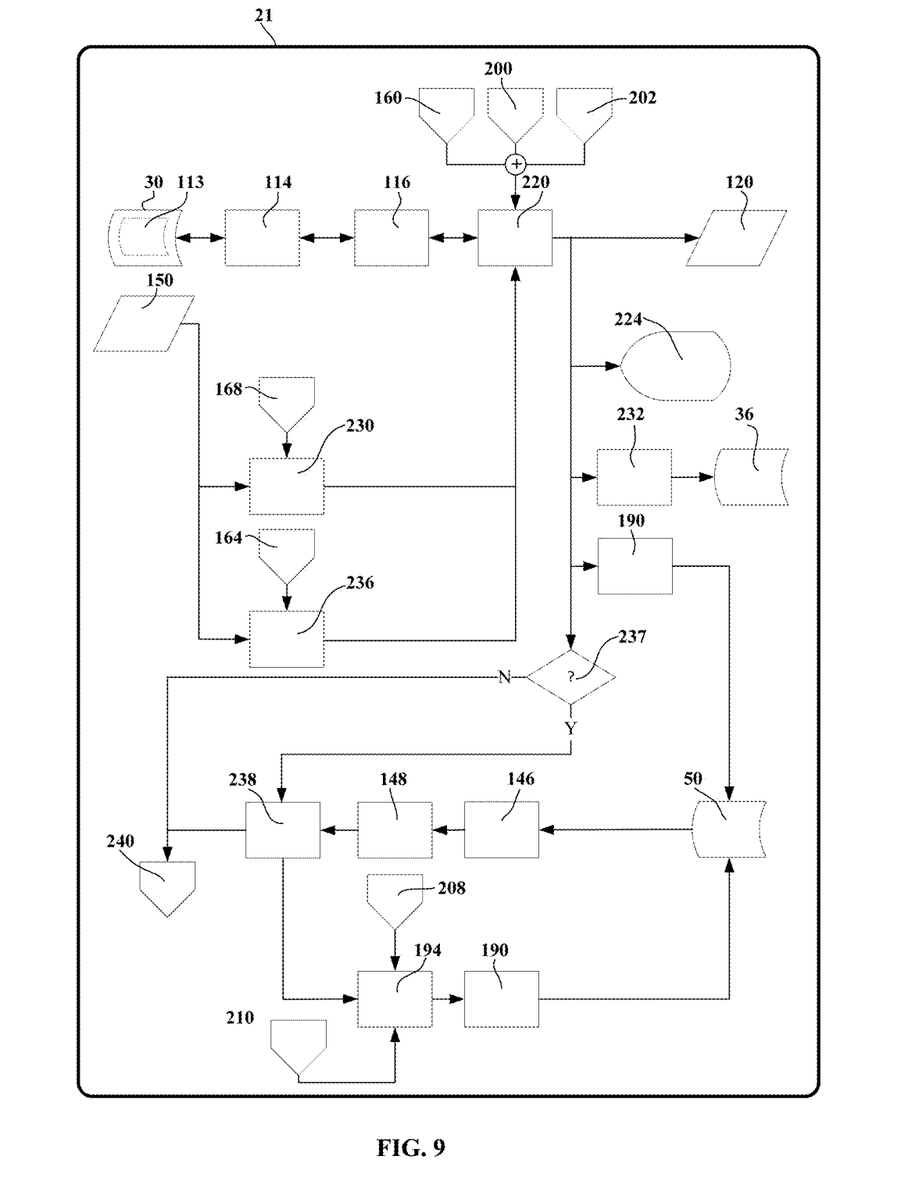
FIG. 9 is a software process flow of special application software operating a distributor's computer used in a networked distributor product programming system that is related to updating the manufacturer's secure product media in one embodiment of the present invention.

In FIG. 7 through FIG. 9 describes the software process flow for the networked DPPS software application 21 from FIG. 4. In FIG. 7 the network DPPS software application starts 140 by presenting the network DPPS welcome and instruction screen 142. A separate process operation directed by the off-page reference to FIG. 8 establishes communicating with the manufacturer's server 144, which is a parallel process activity that will need to complete before the processes in FIG. 7 can complete. The decrypt operational data process 146 retrieves the networked DPPS operational data file 50 as well as performs a decryption of the file contents that the format operational data process 148 transforms into a useful form to the operational data elements temporary storage 150 for use by other processes.

Some of the elements from the networked DPPS operational data file 50 are the following:

a definition of the distributor login requirements the control elements state information for authorizing the networked DPPS software application 21 to have access to the manufacturer's secure product media 30 the protocol attributes for accessing the manufacturer's secure product media 30 the data definition for initializing, configuring, or resetting the manufacturer's secure product media 30.

The networked DPPS operational data file 50 will also serve as a repository for recording the data transactions that occur during the creation or service of the manufacturer's secure product media 30, and recording the history information that accumulated on the manufacturer's secure product media 30 during use of the product or accessory.

The network DPPS application display login 152 of in FIG. 7 presents the possible distributor process levels and requests the login password. The network DPPS application display login process 154 determines the login process level and verifies the entered password associated with the process level. If the password is invalid for the requested process level, the application terminates 156. Otherwise a valid process level state 155 is assigned as read-only, general user, or a super-user process level. A read-only distributor process level allows the distributor to only read the contents of the manufacturer's secure product media 30. The network DPPS application read-only user interface 158 directs the associated processes to the read-only process enabled 160 (off-page reference) operations in FIG. 9. The authorization for the distributor to perform processing that involves modification to the manufacturer's secure product media 30 requires either the normal process enabled 200 or the autonomous process enabled 202 (the off-page reference from FIG. 8) conditions be true. The distributor processing enable state 159 allows the distributor to only read from the manufacturer's secure product media 30 when the normal process enabled 200 and the autonomous process enabled 202 conditions are both false. If either condition is true it enables the networked DPPS software application 21 to have specific access to the manufacturer's secure product media 30 based on the modification process level state 161. During login, the network DPPS application display login process 154 evaluates the modification process level state 161 to determine if the network DPPS general user interface 162 should be presented, or present the network DPPS super-user interface 166. The network DPPS general user interface 162 allows the distributor to update or reset the manufacturer's secure product media 30 that occurs during service. Updating or resetting the manufacturer's secure product media 30 occurs through the off-page reference 164 that directs processing to FIG. 9. The network DPPS super-user interface 166 allows the distributor to create the manufacturer's secure product media 30 that is needed during production of the product or accessory. Creating the manufacturer's secure product media 30 occurs through the off-page reference 168 that directs processing to FIG. 9.

In FIG. 8 the software process flow related to distributor authorization from the manufacturer's DPPS authorization and reporting server 26 (in FIG. 2) for the networked DPPS software application 21 is described. The off-page reference from FIG. 7 starts off the process of communicating with the manufacturer's server 144. The user is presented with a message that the process of network connectivity with the manufacturer 170 is started. The establish manufacturer server connectivity process 172 performs the authentication required for the connection, as well as performs the internet communication protocol. If the manufacturer server connected state 173 indicates no connection, the server connection retry process 174 continually attempts to reestablish manufacturer server connectivity process 172 provided the server connection retry timeout 175 does not occur. If the latter does occur, the user is presented with the prompt of retrying the server connection 176. If the user elects to not retry server connection 177, the autonomous operation confirmation process 194 starts, else the establish manufacturer server connectivity process 172 is restarted. If the manufacturer server connected state 173 indicates a connection, the DPPS server data communication process 178 begins to perform a data exchange with the manufacturer's DPPS authorization and reporting server 26. The DPPS server operational data exchange process 180 controls the direction of data flow from the DPPS server data communication process 178 to the other processes of the networked DPPS software application 21.

In FIG. 8 the synchronize DPPS operational data process 184 extracts the contents of the networked DPPS operational data file 50 to the decrypt operational data process 146 for operational use. The synchronize DPPS operational data process 184 synchronizes the networked DPPS software application 21 to the manufacturer's DPPS authorization and reporting server 26 (in FIG. 2). This process operates in parallel with all other software processes to try and maintain synchronization either through its own intelligence processing or upon request from the manufacturer's server. Periodic synchronization is required to ensure authorization to perform processing of the manufacturer's secure product media 30 is permitted, for instance the manufacturer could immediately stop the distributor from further processing because of distributor quality issues, regulatory issues, or financial issues, etc. Synchronization also ensures the media configuration data for the manufacturer's secure product media 30 is current, and to ensure the manufacturer has received the historical process data collected during the time of the last operation(s). The synchronization data is formatted into a custom protocol by the synchronize DPPS operational data process 184, and then encrypted by the encrypt outgoing network data process 182 that is forwarded to the DPPS server operational data exchange process 180, which buffers and controls the outgoing data to the DPPS server data communication process 178. One of the process control elements of the networked DPPS operational data file 50 is a synchronization time interval limit that defines the maximum time interval allowed between manufacturer to distributor synchronizations. The distributor must comply with the synchronization time interval else the synchronize DPPS operational data process 184 will automatically disable the networked DPPS software application 21 from further processing. Enabling the networked DPPS software application 21 to have access to the manufacturer's secure product media 30 is accomplished through the software application's control element known as the processing state variable that will be discussed in the following section.

In FIG. 8 during the synchronize DPPS operational data process 184, inbound information from the manufacturer's DPPS authorization and reporting server 26 (in FIG. 2) is forwarded from the DPPS server operational data exchange process 180 to the decrypt inbound network data process 186. This latter process decrypts the data and forwards it to the format operational data process 148. The synchronize DPPS operational data process 184 can query the format operational data process 148 to determine if an inbound synchronization request has been made by the manufacturer's server. During the synchronization, it would be possible for the manufacturer to remotely update the networked DPPS software application 21 if the application was not current. The format operational data process 148 also calls on the decrypt operational data process 146 to decrypt the contents of the networked DPPS operational data file 50 so that together with the decrypted data from the decrypt inbound network data process 186 the data can be integrated and formatted into a usable form by the application. The authenticate operational state process 188 evaluates the control elements of the operational data to determine if distributor service or production processing is allowed with the outcome being directed by the authorized operation state 189. An example of operational data elements (refer to Table 4) that could control access to the manufacturer's secure product media 30 is a processing state variable that when its status is set to disabled would disable the networked DPPS software application 21 accessibility. Another operational data element is a transaction (process) counter limit that once it has been reached, it would cause the networked DPPS software application 21 to disable access to the manufacturer's secure product media 30. If the processing state variable is set to enabled and the transaction (process) counter limit has not been reached, the normal process enabled 200 (which connects to FIG. 7) will allow the networked DPPS software application 21 to have specific access privileges to the manufacturer's secure product media 30 based on the modification process level state 161 of FIG. 7. The authenticate operational state process 188 forwards the operational data elements to the encrypt operational data 190 for encryption and transfer to the networked DPPS operational data file 50. If the authorized operation state 189 reports no server connection and the processing state variable is set to disabled, a prompt for the operational data condition 192 occurs allowing the user to retry server connection 177. If the user elects not to retry server connection 177 the autonomous operation confirmation process 194 is initiated. The autonomous operation confirmation process 194 requires the networked DPPS operational data file 50 be read to evaluate the control elements related to autonomous operation. The file is decrypted, using the decrypt operational data process 146, and then formatted into a working database, from the format operational data process 148 to arrive at an autonomous operation authorized state 195. The autonomous operation confirmation process 194 looks at the control element conditions of the processing state variable, the (process) counter limit, and the autonomous operation time limit to determine if the networked DPPS software application 21 can have access to the manufacturer's secure product media 30. If the control element conditions result in the autonomous operation authorized state 195 being disabled, user notification that autonomous operation is not permitted 196 occurs. The autonomous operation confirmation process 194, as an example, compares the autonomous time limit to the period that the networked DPPS software application 21 has operated autonomously. When synchronization occurs with the manufacturer's server this causes the autonomous timer to be reset. If in the autonomous process enabled 202 state (which connects to FIG. 7), this allows specific access to the manufacturer's secure product media 30 based on the modification process level state 161 of FIG. 7. From the continue application state 197 if the user elects to not continue the networked DPPS software application 21 the application terminates 156, otherwise the establish manufacturer server connectivity process 172 restarts.

In FIG. 9 are the software process flow related to access, updating, or creating the manufacturer's secure product media 30. The secure media control interface process 220 controls the processes of reading from, updating, or creating the manufacturer's product media data 113 that is contained within the manufacturer's secure product media 30. The control inputs, read-only process enabled 160 (off-page reference to FIG. 7), normal process enabled 200 (off-page reference to FIG. 8), and autonomous process enabled 202 (off-page reference to FIG. 8), combined with the control inputs from initialize secure media process 230 or the update secure media process 236 determine the level of accessibility to the manufacturer's product media data 113. The manufacturer's secure product media 30 requires authentication to access or update its contents. The authenticate product media process 116, by way of control from the secure media control interface process 220, removes the security data lock. The product media data transfer process 114 controls the communication between the manufacturer's secure product media 30 and the networked DPPS software application 21. Once the manufacturer's secure product media 30 is unlocked, access to the manufacturer's product media data 113 for reading or writing to the media is granted. The media process restriction for the user have read-only access to the manufacturer's product media data 113 is determined by the off-page reference 160 that originated from FIG. 7. The secure media control interface process 220 for reading and updating the manufacturer's secure product media 30 requires that the normal process enabled 200 or autonomous process enabled 202 conditions are true and communicating with the update secure media process 236. During an update, the operational data elements temporary storage 150 is read by the update secure media process 236 for definition of the data values used in updating or resetting the manufacturer's product media data 113. The secure media control interface process 220 for reading and creating the manufacturer's secure product media 30 requires the normal process enabled 200 or autonomous process enabled 202 conditions are true and communicating with the initialize secure media process 230. Using secure media control interface process 220, the authenticate product media process 116 unlocks the manufacturer's secure product media 30 and confirms that it is a valid but uninitialized media. During media initialization, the operational data elements temporary storage 150 is read by the initialize secure media process 230 for definition of the data values used for initializing the manufacturer's product media data 113. The valid process level state 155 from FIG. 7 determined which of the update secure media process 236 or initialize secure media process 230 will execute.

In FIG. 9, during any valid data exchange by the secure media control interface process 220 with the manufacturer's secure product media 30, the contents of the product media temporary storage 120 is updated with the data from the manufacturer's product media data 113, and the data is formatted for presentation to the network DPPS media data display screen 224. The secure media control interface process 220 also forwards any valid data exchange with the manufacturer's secure product media 30 to the format secure media data to database process 232, which writes the result to the service and production records and product application history files 36, and forwards any valid data exchange to the encrypt operational data process 190 for saving to the networked DPPS operational data file 50. When the networked DPPS operational data file 50 is updated, the synchronize DPPS operational data process 184 described for FIG. 8 will detect the update and try to forward the service and production records and product application history files 36 to the manufacturer's DPPS authorization and reporting server 26 (in FIG. 2). If the manufacturer's secure product media 30 was updated or initialized, the secure media processed state 237 forces the update transaction counter process 238 to decrement the (process limit) transaction counter, which is an element of the networked DPPS operational data file 50. To extract the transaction counter element, the decrypt operational data process 146 performs a decryption of the networked DPPS operational data file 50 contents and the decrypted data is then formatted into a usable database from the format operational data process 148. Once the transaction counter process 238 decrements the transaction counter data element, it forwards formatted database the encrypt operational data 190 for encryption and transfer to the networked DPPS operational data file 50.

Figure 10:
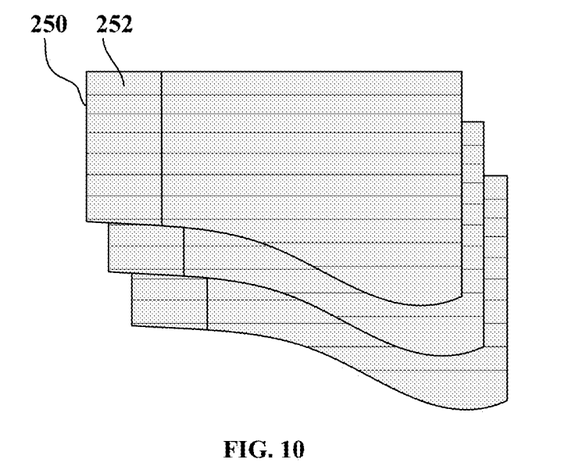
FIG. 10 is a schematic diagram illustrating stored information for a database containing production records and product application history files produced by a licensed distributor product programming system and a networked distributor product programming system in one embodiment of the present invention.

In FIG. 10 is the DPPS local processed database item 250 that describes content examples of the type production records and product application history files 36 saved by the licensed DPPS software application 13 or the networked DPPS software application 21 referred to in FIG. 3, FIG. 4, FIG. 6, and FIG. 9. The processed database field number 252 is the unique database elements that comprise each type of data table within the database. The processed database field number 252 can also serve as a key field for searches and sorting within the database. The following tables 1 through 3 are examples of the types of data elements stored by the manufacturer's secure product media 30, and that are retrieved during reprocessing or in producing the manufacturer's product or accessory. The data elements listed in the tables are an example of an accessory that is used clinically to perform therapy or treatment, and has the attributes of energy, frequency, and a dose element associated with it. There could be other types of attributes used to define the tables so that the accessory or product could be controlled or limited during its intended use. The data in tables 1 through 3 can be used by the manufacturer to generate reports for accounting functions, regulatory reporting requirements and verification of distributor process records as needed.

The types of elements In Table 1 is the transaction data that occurs when the manufacturer's secure product media 30 was updated or created during the accessory reprocessing or production, respectively; there would be one of the following table records per each reprocessing or production event. The field items in Table 1 could serve as an audit record that identifies the product or accessory, its application limits, application history, and historical information related to service or maintenance.

TABLE 1

| Field No. | Description |
|---|---|
| 1 | DPPS workstation ID/Programming unit ID |
| 2 | Accessory serial number |
| 3 | Accessory model number |
| 4 | Transaction Code (L = Read, S = Program, N = New, or V = View Data) |
| 5 | Last maintenance date (format mm/dd/yyyy) |
| 6 | Last maintenance time (format hh:mm:ss) |
| 7 | Country Code |
| 8 | Maximum energy level limit for accessory |
| 9 | Lifespan (maximum number of therapies or treatments allowed) |
| 10 | Maximum frequency (in Hz) limit for accessory |
| 11 | Expiration period (in months) |
| 12 | Number of maintenances/refurbishments performed |
| 13 | Total number of Errors (history) |
| 14 | Total number of therapies or treatments applied since last reprocessing |
| 15 | First accessory use (format mm/dd/yyyy) |
| 16 | Last accessory use date (format mm/dd/yyyy) |
| 17 | Last associated product ID serial number |
| 18 | User (reprocessing technician) ID number |
| 19 | User (reprocessing technician) name |
| 20 | User Type (N = Normal, A = Administrator, or S = Super-User) |
| 21 | Remaining lifespan (only from L or V transaction code) |
| 22 | Future Use . . . |
| . . . | . . . |

In Table 2 is an example of another type of transaction data that occurs when the manufacturer's secure product media 30 was reprocessed. This information describes the accessory or product use e.g. clinical history. There would be one of the following table records per each therapy or clinical event. Table 2 shows field items describing the energy, frequency, and dose applied to a patient during their therapy, along with system identification details. System identification details could be expanded so that the Manufacturer could electronically track materials (via bar-coding, RFID identification, etc.) being utilized by the Distributor to perform the reprocessing or servicing, or production and thereby facilitating remote inventory management.

TABLE 2

| Field No. | Description |
|---|---|
| 1 | DPPS workstation ID/Programming unit ID |
| 2 | Accessory serial number |
| 3 | Associated product ID serial number |
| 4 | Therapy date (format mm/dd/yyyy) |
| 5 | Therapy time (format hh:mm:ss) |
| 6 | Therapy/Treatment Number |
| 7 | Total dose delivered |
| 8 | Frequency level |
| 9 | Energy level |
| 10 | Accessory type |
| 11 | Treated area (inches sq. or mm sq.) |

TABLE 2-continued

| Field No. | Description |
|---|---|
| 12 | Future Use . . . |
| . . . | . . . |

In Table 3 is another type of transaction data that occurs when the manufacturer's secure product media 30 was reprocessed. This information is related to the accessory or product errors that occurred during its use. There would be one of the following table records per each error event.

TABLE 3

| Field No. | Description |
|---|---|
| 1 | DPPS workstation ID/Programming unit ID |
| 2 | Accessory serial number |
| 3 | Associated product ID serial number |
| 4 | Error code |
| 5 | Error event date (format mm/dd/yyyy) |
| 6 | Error event time (format hh:mm:ss) |
| 7 | Future Use . . . |
| . . . | . . . |

Figure 11:
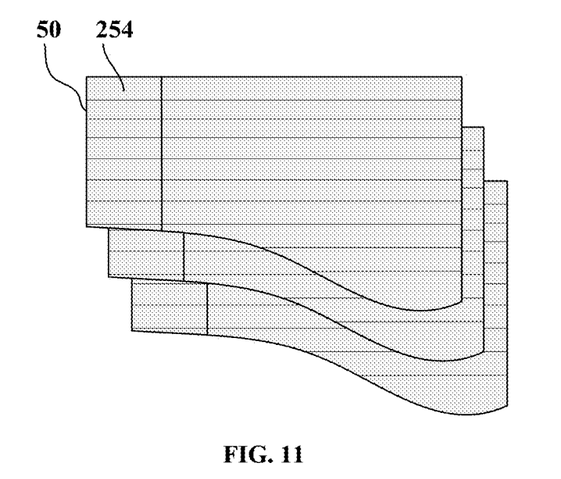
FIG. 11 is a schematic diagram illustrating a operational data file that is needed by a networked distributor product programming system in one embodiment of the present invention.

In FIG. 11 is an example of the networked DPPS operational data file 50 contents. The networked DPPS operational database field number 254 is the unique database elements that comprise each type of data table within the database. The networked DPPS operational database field number 254 can also serve as a key field for searches and sorting within the database.

The Tables 1 through 4 are examples of the types of database tables and elements contained in the networked DPPS operational data file 50 and maintained by the networked DPPS software application 21. The database Tables 1 through 3 would be stored in the networked DPPS operational data file 50 at the time of processing when communication with the manufacturer's server could not be established. During the data synchronization process discussed in FIG. 9 the database Tables 1 through 3 would be transferred to the manufacturer's DPPS authorization and reporting server 26 (in FIG. 2) and then could be removed from the networked DPPS operational data file 50. Other possible embodiment is the database tables can be a shared file that resides on the DPPS authorization and reporting server 26, or what has been described previously as a copy of the file stored on the distributor's DPPS workstation 12.

The information in Table 4 would be used by the networked DPPS software application 21 to connect to the manufacturer's server and control the accessibility of the software application to the manufacturer's secure product media 30. The table fields 1 and 3 are needed in connection to the DPPS authorization and reporting server 26. The fields 4 through 14 control the networked DPPS software application 21 flow. The field 13 is a region code used by the DPPS authorization and reporting server 26 to only allow the distributor to modify the manufacturer's secure product media 30 for country specific product accessories.

TABLE 4

| Field No. | Description |
|---|---|
| 1 | DPPS workstation ID/Programmer unit ID |
| 2 | IP Address for DPPS authentication server |
| 3 | DPPS Software version and identification |
| 4 | Processing state status (e.g. 0 = Disabled, 1 = Enabled) |

TABLE 4-continued

| Field No. | Description |
|---|---|
| 5 | Synchronization interval limit (in hours) |
| 6 | Last connection state (e.g. 0 = Autonomous, 1 = Connected, 2 = Remote) |
| 7 | Last processing date (format mm/dd/yyyy) |
| 8 | Last processing time (format hh:mm:ss) |
| 9 | Last synchronization date (format mm/dd/yyyy) |
| 10 | Last synchronization time (format hh:mm:ss) |
| 11 | Transaction quantity limit or process limit of refurbishments allowed |
| 12 | Current transaction quantity or process quantity |
| 13 | Autonomous operation time limit |
| 14 | Region Code |
| 15 | Future Use . . . |
| . . . | . . . |

The information in Table 5 would be used by the DPPS server software application 27 operating the DPPS authorization and reporting server 26 to connect to the distributor's DPPS workstation 12 and control the accessibility of the distributor's networked DPPS software application 21 to the manufacturer's secure product media 30. During synchronization, the information in Table 5 except for the IP address for DPPS workstation would mirror the information in Table 4.

TABLE 5

| Field No. | Description |
|---|---|
| 1 | DPPS workstation ID/Programmer unit ID |
| 2 | IP address for DPPS workstation |
| 3 | Processing state status (0 = Disabled, 1 = Enabled) |
| 4 | Synchronization interval (in hours) |
| 5 | Last connection state (0 = Autonomous, 1 = Connected, 2 = Remote, 3 = Bypass) |
| 6 | Last processing date (format mm/dd/yyyy) |
| 7 | Last processing time (format hh:mm:ss) |
| 8 | Last synchronization date (format mm/dd/yyyy) |
| 9 | Last synchronization time (format hh:mm:ss) |
| 10 | Transaction quantity limit or process limit of refurbishments allowed |
| 11 | Current transaction quantity or process quantity |
| 12 | Autonomous operation time limit |
| 13 | Region Code |
| 14 | Future Use . . . |
| . . . | . . . |

While the invention has been described with reference to exemplary structures and methods in embodiments, the invention is not intended to be limited thereto, but to extend to modifications and improvements within the scope of equivalence of such claims to the invention.

What we claim is:

1. A system for controlling and monitoring service activities of an authorized distributor for a product of a manufacturer comprising:

a product including a hardware security device that only permits authorized operation of the product for a predetermined number of uses before disabling normal operation of the product and requiring authorization to permit further use when the predetermined number of uses is reached, wherein the predetermined number of uses is based on at least one service activity of an authorized distributor of the product that includes required maintenance, part refurbishment, part replacement, reprocessing and production activity for the product; and a product programming interface hardware unit having computer-readable storage memory programmed with reset instructions for product service authorization that is communicatively coupled to the hardware security device and to a computing device running an application program having proprietary access to authenticate and authorize the authorized distributor to conduct the at least one service activity through the application program accessing a license file having a predetermined number of distributor service activity transactions supplied by the manufacturer and stored on secure storage media of the product programming interface hardware unit and upon confirmation by the application program that there are one or more distributor service activity transactions remaining permits the distributor as part of providing the at least one service activity to unlock and cause the reset instructions to be provided from the programming interface hardware unit to the hardware security device of the product, wherein said reset instructions add a further number of authorized uses of the product to the security device.

2. The system of claim 1, wherein the computing security device is selected from the group consisting of a SIM card, secure memory device, and security key.

3. The system of claim 2, wherein the product is a medical treatment device.

4. The system of claim 3, wherein the medical treatment device includes a serviced element of a shock wave applicator.

5. The system of claim 1, wherein the product is a medical treatment device.

6. The system of claim 5, wherein the medical treatment device includes a serviced element of a shock wave applicator.

7. The system of claim 6, wherein the license file includes one or more information elements for authentication and authorization by the application program selected from the group consisting of unique distributor's machine identification, license issue number, transaction limit for the number of manufacturer's products where service or maintenance has been performed, a production quantity limit to the manufacturer's products or accessories produced by the distributor, and a license expiration period.

8. The system of claim 5, wherein the license file includes one or more information elements for authentication and authorization by the application program selected from the group consisting of unique distributor's machine identification, license issue number, transaction limit for the number of manufacturer's products where service or maintenance has been performed, a production quantity limit to the manufacturer's products or accessories produced by the distributor, and a license expiration period.

9. The system of claim 1, wherein the license file includes one or more information elements for authentication and authorization by the application program selected from the group consisting of unique distributor's machine identification, license issue number, transaction limit for the number of manufacturer's products where service or maintenance has been performed, a production quantity limit to the manufacturer's products or accessories produced by the distributor, and a license expiration period.

10. A system for controlling and monitoring service activities of an authorized distributor for a product of a manufacturer comprising:

a product including a hardware security device that only permits authorized operation of the product for a predetermined number of uses before disabling normal operation of the product and requiring authorization to permit further use when the predetermined number of uses is reached, wherein the predetermined number of uses is based on at least the service activity of an authorized distributor of the product that includes required maintenance, part refurbishment, part replacement, reprocessing and production activity for the product; and a product programming hardware interface unit having computer-readable storage memory programmed with reset instructions for product service authorization that is communicatively coupled to the hardware security device and to a computing device running an application program having a wide area network connection to a server software application of the manufacturer on a remote server that remotely authenticates and authorizes the authorized distributor to conduct the at least one service activity and permits the authorized distributor through the application program to unlock and cause the reset instructions to be provided from the programming interface hardware unit to the hardware security device of the product, wherein said reset instructions add a further number of authorized uses of the product to the security device.

11. The system of claim 10, wherein the computing security device is selected from the group consisting of a SIM card, secure memory device, and security key.

12. The system of claim 11, wherein the product is a medical treatment device.

13. The system of claim 10, wherein the product is a medical treatment device.

14. The system of claim 13, wherein the medical treatment device includes a serviced element of a shock wave applicator.

15. The system of claim 12, wherein the medical treatment device includes a serviced element of a shock wave applicator.

16. The system of claim 10, wherein the server software application includes at least one criteria for determining whether to permit the distributor to conduct the at least one service activity selected from the group consisting of process quantity limit, date controlled limit and terminated at will by the manufacturer.

17. The system of claim 13, wherein the server software application includes at least one criteria for determining whether to permit the distributor to conduct the at least one service activity selected from the group consisting of process quantity limit, date controlled limit and terminated at will by the manufacturer.

18. The system of claim 10, wherein the server software application is configured to retrieve one or more information elements from an operational data file for authenticating and authorizing the authorized distributor to conduct the at least one service activity selected from the group consisting of a definition of distributor login requirements, information for authorizing the application program to access the security device, protocol attributes for accessing the security device, and data definition for initializing, configuring or resetting the security device.

19. The system of claim 13, wherein the server software application is configured to retrieve one or more information elements from an operational data file for authenticating and authorizing the authorized distributor to conduct the at least one service activity selected from the group consisting of a definition of distributor login requirements, information for authorizing the application program to access the security device, protocol attributes for accessing the security device, and data definition for initializing, configuring or resetting the security device.

20. The system of claim 14, wherein the server software application includes at least one criteria for determining whether to permit the distributor to conduct the at least one service activity selected from the group consisting of process quantity limit, date controlled limit and terminated at will by the manufacturer.

\* \* \* \* \*